United States Patent
Vargas Fonseca (10) Patent No.: US 11,602,584 B2
(45) Date of Patent: Mar. 14, 2023

(54) SYSTEM FOR MONITORING PHYSIOLOGICAL PARAMETERS IN EXTRACORPOREAL CIRCULATION

(71) Applicant: ZAMMI INSTRUMENTAL LTDA, Duque de Caxias (BR)

(72) Inventor: Luiz Henrique Vargas Fonseca, Duque de Caxias (BR)

(73) Assignee: ZAMMI INSTRUMENTAL LTDA, Duque de Caxias (BR)

( * ) Notice: Subject to any disclaimer, the term of this patent is extended or adjusted under 35 U.S.C. 154(b) by 518 days.

(21) Appl. No.: 16/487,534

(22) PCT Filed: Feb. 9, 2018

(86) PCT No.: PCT/BR2018/050030
§ 371 (c)(1),
(2) Date: Oct. 29, 2019

(87) PCT Pub. No.: WO2018/152606
PCT Pub. Date: Aug. 30, 2018

(65) Prior Publication Data
US 2020/0061278 A1    Feb. 27, 2020

(30) Foreign Application Priority Data

Feb. 22, 2017 (BR) .................... 10 2017 0003716 9

(51) Int. Cl.
*A61M 1/36* (2006.01)
(52) U.S. Cl.
CPC ........ *A61M 1/3639* (2013.01); *A61M 1/3666* (2013.01); *A61M 2205/502* (2013.01); *A61M 2230/50* (2013.01)

(58) Field of Classification Search
CPC .............. A61M 1/3639; A61M 1/3666; A61M 2205/502; A61M 2230/50
(Continued)

(56) References Cited

U.S. PATENT DOCUMENTS 5,993,395 A    11/1999   Shulze
6,315,751 B1   11/2001   Cosgrove et al.
(Continued)

FOREIGN PATENT DOCUMENTS

JP    S60102003 U    7/1985
JP    H0523393 A     2/1993
(Continued)

OTHER PUBLICATIONS

PENDOTECH. PendoTECH PressureMat System, versao PMSSREV6, published in 2016, online, available in <https://web.archive.org/web/20160807041027/http://www.pendotech.com/products/PressureMAT/PressureMAT_Spec_Sheet.pdfl. Accessed on May 16, 2018. (the whole document).
(Continued)

*Primary Examiner* — Phillip A Gray
(74) *Attorney, Agent, or Firm* — Nixon & Vanderhye, P.C.

(57) ABSTRACT

The present invention relates to an integrated system for monitoring physiological variables in cardiopulmonary bypass process, which utilizes a transducer specifically intended to act directly on the cardiopulmonary bypass. Said system according to the present invention comprises at least two components, one is a CPB transducer and a minimonitor, coupled to each other by means of a cable and an electrical connector.

10 Claims, 7 Drawing Sheets

(58) Field of Classification Search
USPC .......................................................... 604/27
See application file for complete search history.

(56) References Cited

U.S. PATENT DOCUMENTS

| | | |
|---|---|---|
| 2003/0135152 A1 | 7/2003 | Kollar et al. |
| 2008/0053255 A1* | 3/2008 | Furey .................... G01D 11/30 73/866.5 |
| 2012/0041256 A1* | 2/2012 | Large .................. A61M 1/3667 600/16 |

FOREIGN PATENT DOCUMENTS

| | | |
|---|---|---|
| JP | H06213732 A | 8/1994 |
| JP | 2007105459 A | 4/2007 |
| JP | 2009521984 A | 6/2009 |
| JP | 2014133174 A | 7/2014 |
| JP | 2015130977 A | 7/2015 |
| JP | 2015227856 A | 12/2015 |

OTHER PUBLICATIONS

PENDOTECH. PendoTECH Single Use Pressure Sensors, versao PSSS-REV3, published in 2016, online, available in <https ://web . archive . org/web/20160807041027/http ://www.pendotech.com/products/disposable_pressure_sensors/Pressure_Sensors_Spec_Sheet.pdf. Accessed on May 16, 2018.

\* cited by examiner

SYSTEM FOR MONITORING PHYSIOLOGICAL PARAMETERS IN EXTRACORPOREAL CIRCULATION

This application is the U.S. national phase of International Application No. PCT/BR2018/050030 filed Feb. 9, 2018 which designated the U.S. and claims priority to BR Patent Application No. 10 2017 0003716 9 filed Feb. 22, 2017, the entire contents of each of which are hereby incorporated by reference.

FIELD OF THE INVENTION

The present invention is an integrated system for monitoring physiological variables in cardiopulmonary bypass process, which uses a pressure transducer specifically intended to actuate directly on the cardiopulmonary bypass.

BACKGROUND OF THE PRIOR ART

One of the currently most commonly used techniques for cardiac surgery is cardiopulmonary bypass, also known as "CPB". With this technique it is possible to promote circulatory and ventilatory support to the patient and induce cardioplegia, stage in which the heartbeat is suppressed so as the surgeon may more easily perform the different heart surgery. Blood flow is kept by a mechanical pump coupled to a cardiopulmonary bypass. The cardiopulmonary bypass is quite complex and contains several devices, such as oxygenator, venous reservoir, arterial filter, etc., which provide, together with the pump, the blood flow and oxygenation necessary for the maintenance of the patient's life during surgery. Cardiopulmonary bypass is a high-risk procedure which requires careful monitoring of the patient's physiological parameters.

According to the Standards and Guidelines For Perfusion Practice of American Society of ExtraCorporeal Technology, it is highly recommended the pressure and temperature monitoring at several points at the cardiopulmonary bypass. However, the currently available pressure and temperature monitors and transducers are intended for monitoring the patient's vital signs, which are quite different parameters from the pressure and temperature signals present in the cardiopulmonary bypass.

The following table illustrates the value range that patient monitors typically work with and the value range required for monitoring during a cardiopulmonary bypass.

| Parameter | Patient Monitor | CPB Monitor |
| --- | --- | --- |
| Pressure | −10 to 300 mmHg | −400 to +999 mmHg |
| Temperature | 20 to 45° C. | −20 to 50° C. |

As seen, in addition to the insufficient value range, there are commonly problems in adapting sensors available on the market, as these are designed to monitor patient pressure and temperature rather than the cardiopulmonary bypass. In the case of the pressure transducer, for example, there are two types available on the market.

A mechanical pressure transducer, also known as a pressure isolator, is a dome made up of two halves with a connector on each side and a flexible membrane dividing the two compartments. This type of transducer should be connected to the arterial line of the CPB circuit through a luer connector and should be filled with fluid on the side that is connected to the arterial line. The other half should be left filled with air and connected to a mercury or aneroid-type pressure gauge. This type of transducer has a number of drawbacks. A first drawback relates to the difficulties in assembly, which requires filling one side of the membrane with saline and positioning the membrane properly, otherwise pressure measurement may be compromised. A second drawback relates to the fact that due to the high pressures, it is common for blood to enter the dome, which can cause clotting and disrupt the pressure reading. And a third drawback relates to the damping of the pressure wave, that is, due to the nature of the device it is only possible to measure the average pressure in the circuit, which can lead to wrong conclusions, as in roller pumps, for example, it is common to have pressure peaks which are not identified by this type of system. Other drawbacks are still noted in this type of transducer.

The disposable electronic pressure transducer is the second known type on the market and currently is the most modern for patient pressure monitoring. It consists of a dome with a built-in electronic sensor equipped with a cable with an electrical connector at one end which should be connected to an external pressure monitor. However, this transducer also has some drawbacks for pressure measurement during CPB as it was not specifically designed to monitor pressure in the cardiopulmonary bypass circuit. For example, the electronic pressure transducer is supplied in a circuit containing, besides the transducer itself, extensions, 3-way stopcocks for zeroing the monitor, a serum tubing set and a flush device. The transducer is connected to the circuit through a non-compliant extension, which in turn is connected to a luer lock connector. The transducer circuit must be filled with saline so that pressure can be transmitted to the transducer. Another drawback concerns the flush device provided with the transducer, which must be connected to a saline bag pressurized at 300 mmHg in order to avoid blood backflowing into the transducer line. However, as it is common for the pressure in the CPB circuit to exceed 300 mmHg, when this happens there will be blood backflow in the line with subsequent clotting, making it difficult to monitor the pressure. In addition, the function of the flush device is to keep a flush of 3_mL/hr. through the transducer circuit to prevent blood clotting at the circuit end. This flow is obtained through the pressure gradient between the patient pressure (usually 120/80 mmHg) and the 300_mmHg provided by the pressure bag. However, during cardiopulmonary bypass, even when the pressure does not exceed 300_mmHg, the pressure gradient is greatly reduced, causing no flush through the circuit, which can lead to clotting even if there is no backflow. Yet another disadvantageously relevant aspect of the electronic pressure transducer used in CPB is the fact that as the transducer is connected to the CPB circuit through a serum-filled access, there is a liquid column between the transducer and the measurement point. In case of patient pressure monitoring, the transducer should be level with the patient's midaxillary line to counteract the effect of this liquid column on the measured pressure value. However, in the CPB circuit there is no reference point, this reference is the atmospheric pressure itself. Since the measurement points may be at different heights, the difference in height between the measurement point and the transducer fixing point must be taking into account when assessing the pressure measured, otherwise there may be an error interpreting the values measured.

Also, in CPB procedures, temperature sensors are used which are mostly reusable type that cannot be placed directly into contact with blood in the CPB circuit. Thus, disposable adapters are generally used to thermally couple the reusable sensor to the blood at the measurement point. These adapters, in addition to be difficult to access on the market, also introduce a measurement error due to the thermal coupling between the sensor and the adapter. In addition, temperature sensors are often of poor durability and may have read errors over their lifetime.

BRIEF DESCRIPTION OF THE INVENTION

Aiming to solve the above-mentioned drawbacks, besides providing an integrated system to monitor physiological variables in the process of cardiopulmonary bypass—CPB.

The system according to the present invention thus comprises three basic components, namely, a disposable CPB transducer, a minimonitor and an optional central monitor which can be coupled to the minimonitor. Said CPB transducer can be produced in three versions, one pressure-only transducer, one pressure and temperature transducer, or a temperature-only transducer.

BRIEF DESCRIPTION OF THE DRAWINGS

The integrated system for monitoring physiological variables in cardiopulmonary bypass (CPB) process according to the present invention will be better understood by the description of the accompanying illustrative figures, which are illustrated by way of example only, and it will be appreciated by those skilled in the art that several other embodiments may be undertaken without, however, departing from the scope and inventive concept described below. Thus, we have the following.

DETAILED DESCRIPTION OF THE INVENTION

Figure 1:
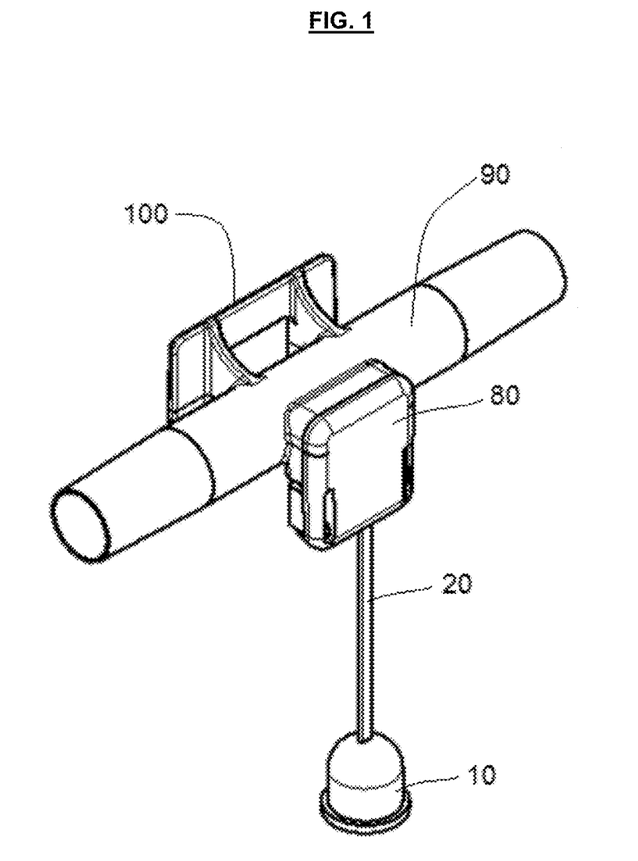
FIG. 1 is a schematic view of the CPB pressure transducer according to the system object of the present invention.
Figure 5:
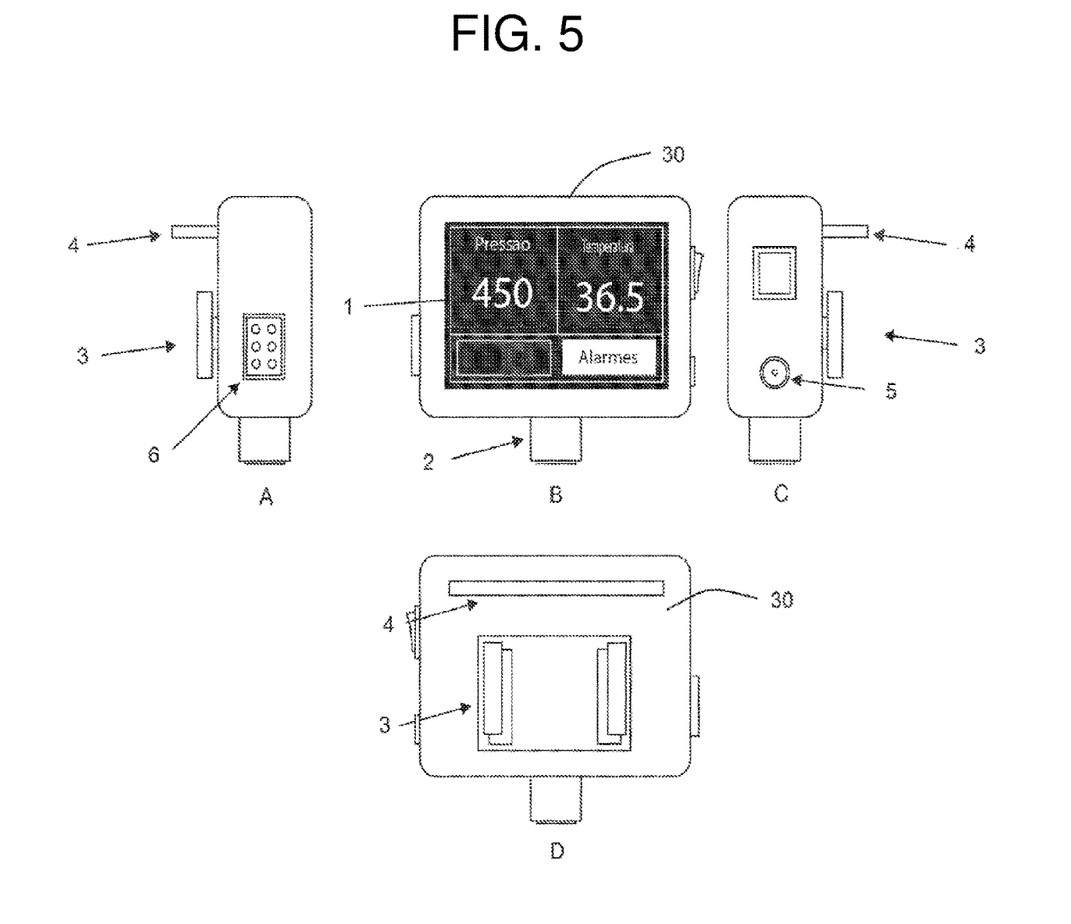
FIGS. 5A-5D are schematic left side, front side, right side and rear side views, respectively, of the minimonitor of the system object of the present invention.

The minimal system for monitoring physiological parameters in cardiopulmonary bypass according to the present invention comprises basically two components, a CPB transducer (110), illustrated in FIG. 1, comprising sensor compartment (80), a connection cable (20), an electrical connector (10), a housing (90), available in several gauges to allow connection to the several pipe gauges existing in the CPB circuits, and an optional fitting (100) for fixing the assembly on the back of a minimonitor (30), illustrated by FIG. 5.

Figure 2:
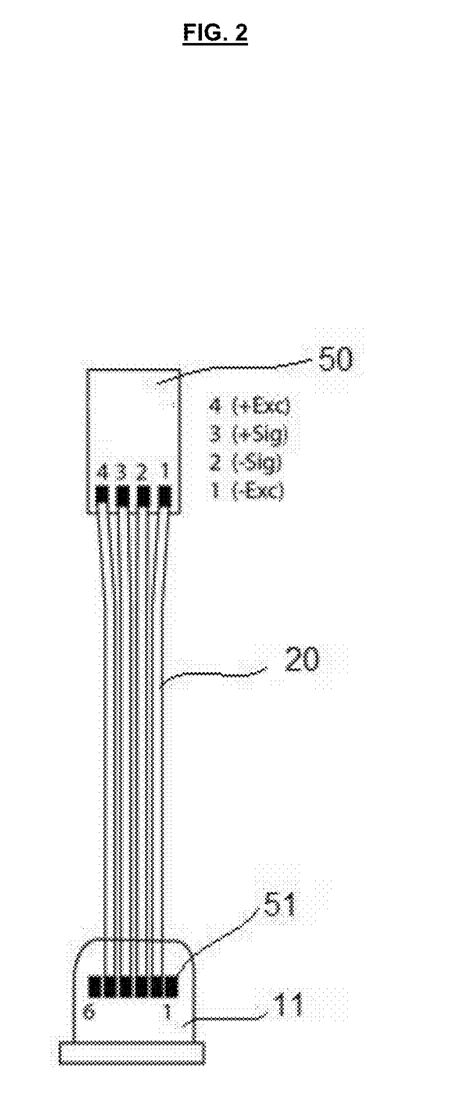
FIG. 2 is an electrical diagram of the CPB pressure transducer according to the system object of the present invention.

In FIG. 2 the wiring diagram of said CPB transducer (110) can be seen with a disposable pressure sensor (51), which is installed inside the sensor compartment (80), which is in direct contact with the patient's blood through a hole in the housing (90), said disposable pressure sensor (51) connecting to the electrical connector (10) of the CPB transducer (110) by a set of cables (20). Thus, we can measure the pressure directly in the CPB circuit.

In this configuration, the system for monitoring physiological parameters in cardiopulmonary bypass in accordance with the present invention allows to achieve a number of advantages over the prior art, among which it is highlighted:

extremely simple assembly as it is sufficient to cut the pipe where the pressure is to be measured and to insert the CPB transducer (110) into place;

there is no need to primer the transducer as it is inserted directly into the CPB circuit itself.

there is no risk of clotting in the transducer, as blood flows continuously through it and there is no stagnation point, or restriction to flow;

there is no need to level the pressure transducer as there is no fluid column between the transducer and the measurement point;

direct electrical connection to the pressure monitor, reducing read errors due to noise and electrical interference in the transducer signal;

real time measurement without damping;

measurement of the actual pressure at the measurement point as the reference is atmospheric pressure;

lower cost compared to conventional transducer, as there is no need for extra components such as stopcocks, flush device, pressure lines, serum tubing set and pressure bag.

Figure 3:
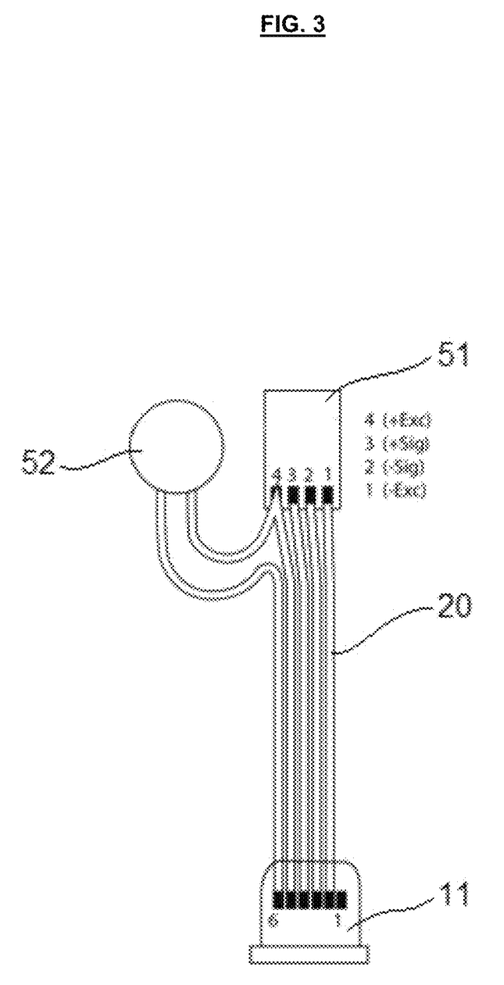
FIG. 3 is an electrical diagram of a second embodiment of the CPB pressure and temperature transducer according to the system object of the present invention.

In another embodiment shown in FIG. 3, the CPB transducer (110) may also include a disposable temperature sensor (52). With this insertion, the system for monitoring physiological parameters in cardiopulmonary bypass in accordance with the present invention further allows to achieve:

real-time temperature measurement at the measurement point with no need for adapters;

lower error and higher measurement speed, since the sensor is in direct contact with blood in the circuit, with no errors or delays due to thermal coupling;

pressure and temperature signals in the same electrical connector (10) for facility and convenience;

greater reliability, because each surgery we have new sensors, which ensures greater accuracy in reading;

lower cost because the two sensors are incorporated in the same housing, including only one cable and only one electrical connector.

Figure 4:
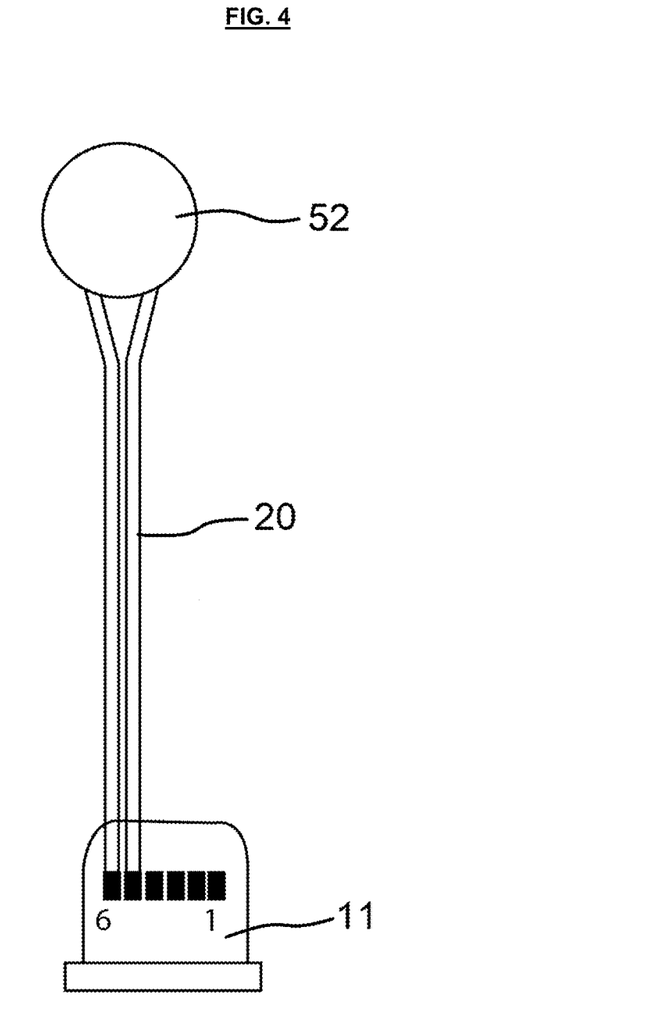
FIG. 4 is an electrical diagram of a third embodiment of the CPB temperature transducer according to the system object of the present invention.

In yet another alternative embodiment, the CPB transducer (110) may have only the temperature sensor (52) for those procedures where only temperature measurement and control is required.

It should be noted that in the three embodiments illustrated in FIGS. 2, 3 and 4 the CPB transducer (110) of the system according to the present invention utilizes the same electrical connector (10) to ensure greater system flexibility and compatibility as a whole.

As stated above, usually the only pressure and temperature monitor available in the operating room is the vital signs monitor used by the anesthetist. In addition to already having the pressure and temperature channels occupied with the patient parameters, this monitor does not reach the required range for pressure and temperature monitoring during CPB, as explained above.

In order to solve this problem and provide the perfusionist with a simple and inexpensive means to enable pressure and temperature monitoring during CPB, the system for monitoring physiological parameter in cardiopulmonary bypass according to the present invention provides a pressure and temperature minimonitor (30) that is directly coupled to the CPB transducer (110), providing continuous readings of average pressure and temperature circuit with no need for any other accessories.

Said minimonitor (30), illustrated in FIGS. 5A-5D, has an analog electronic circuit for amplifying and filtering the pressure and temperature signals from the disposable sensor and a CPU processes and convert to digital the analog signals for later display through a display (1) on the equipment panel and digital transmission to an optional external monitor (not shown). It should be noted this minimonitor (30) is compatible with the three CPB transducer (110) models described above according to FIGS. 2, 3 and 4, respectively, pressure, temperature and pressure and temperature. Furthermore, said minimonitor (30) is also compatible with conventional pressure transducers. Furthermore, said minimonitor (30) does not require any configuration. Simply connect the CPB transducer (110) or alternatively a conventional pressure transducer to the minimonitor (30) and it will display the values for available sensors, pressure, pressure and temperature or temperature only.

In addition, the minimonitor (30) can be powered from an external source or a battery, or even through digital communication cables when connected to the external monitor (not shown), dispensing the external power supply.

Structurally, said minimonitor (30) comprises a display (1) for displaying pressure and/or temperature values and user interface, an electrical connector (2) for connection to the CPB transducer (110), and may optionally have an extension for better positioning. At the rear, said minimonitor (30) has a fitting (3) for direct coupling to the CPB transducer (110) or circuit tube and an auxiliary clamp fitting (4). The minimonitor (30) also has a connector (5) for external power supply and a connector (6) for the communication cable with the central monitor.

The minimonitor (30) according to the present invention has the following preferred technical characteristics: continuous monitoring of average pressure with a range of –400 to +999 mmHg; continuous temperature monitoring with a range between –20 and +50° C.; barograph for displaying instant pressure changes; visual and sound alarms for pressure and temperature; fitting for direct coupling to CPB transducer (10) or auxiliary clamp.

Additionally, said minimonitor (30) has direct electrical coupling to the CPB transducer (110), with no need for intermediate cables, which improves signal-to-noise ratio and reduces signal interference, improving quality and reliability of the signal coming from the transducer and hence the accuracy and reliability of pressure and temperature readings. It also includes automatic zero system as described in another patent of same author, dispensing pressure transducer zeroing and allowing direct connection of the transducer to the CPB circuit, besides having extremely simple operation, simply by connecting the external power supply or installing the battery and turn on the minimonitor (30) and monitoring will start in a moment.

As described above, for most situations, the pressure and temperature minimonitor (30) will likely meet the perfusionist's needs, but in some situations such as ECMO procedures, surgeries with pumps providing pulsatile flow or longer and more complex surgeries, additional information or resources may be required, such as pressure curves, systolic and diastolic pressure values, hydraulic resistance calculations, trend charts, alarms, etc. In order to meet these specific situations, the minimonitor (30) is provided with a connector for digital communication, through which it sends data such as systolic, diastolic and mean pressure, and temperature values to an external monitor (40), illustrated in FIG. 6. This external monitor (40), in turn, is capable of receiving data from multiple minimonitors (30, 30', 30", 30''') and displaying them graphically and numerically in conjunction with, at the same display, also having the ability to perform several calculations, such as the hydraulic resistance calculation which will be explained below, and it also has other features common to the vital signs monitors available on the market, such as visual and sound alarms, among others.

Figure 6:
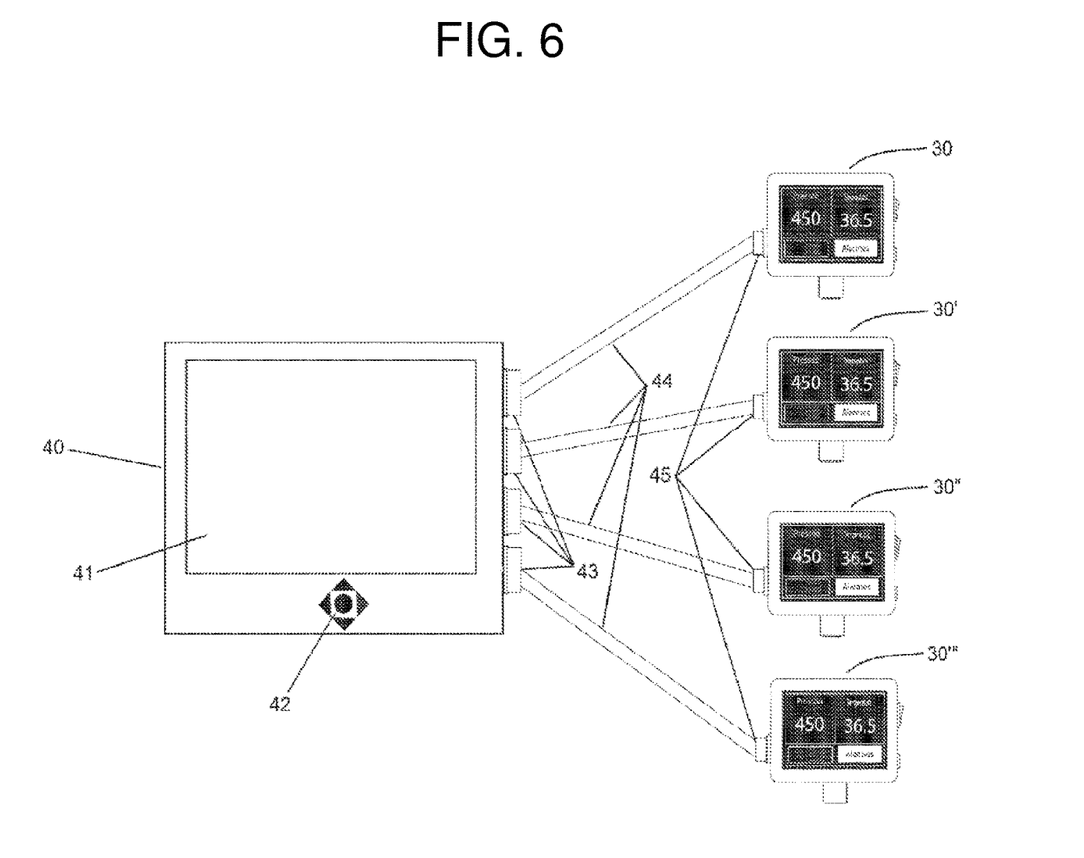
FIG. 6 is a schematic view of the compact central module of the system object of the present invention.

According to the system for monitoring physiological parameters in cardiopulmonary bypass according to the present invention, said external monitor (40), when connected to the minimonitor (30), besides receiving the data for display on the screen, provides it with the power needed for its operation, without the use of external sources or batteries. Said external monitor (40) may be comprised of a single compact unit with CPU, user interface and display, or may consist of a module containing the CPU and user interface control panel and an external video monitor coupled through video cable for greater flexibility in operating room positioning and greater user convenience.

Importantly, the use of said external monitor (40) is not restricted to pressure and temperature transducers and can be used with other sensors such as online flow and oximetry sensors or even other equipment compatible with the communication protocol of said external monitor (40).

Structurally, the compact external monitor (40) according to the present invention has a display (41) and control buttons (42) for interaction with the software. It has connectors (43) and digital communication cables (44) for connection to the connectors (45) of the minimonitor (30).

Figure 7:
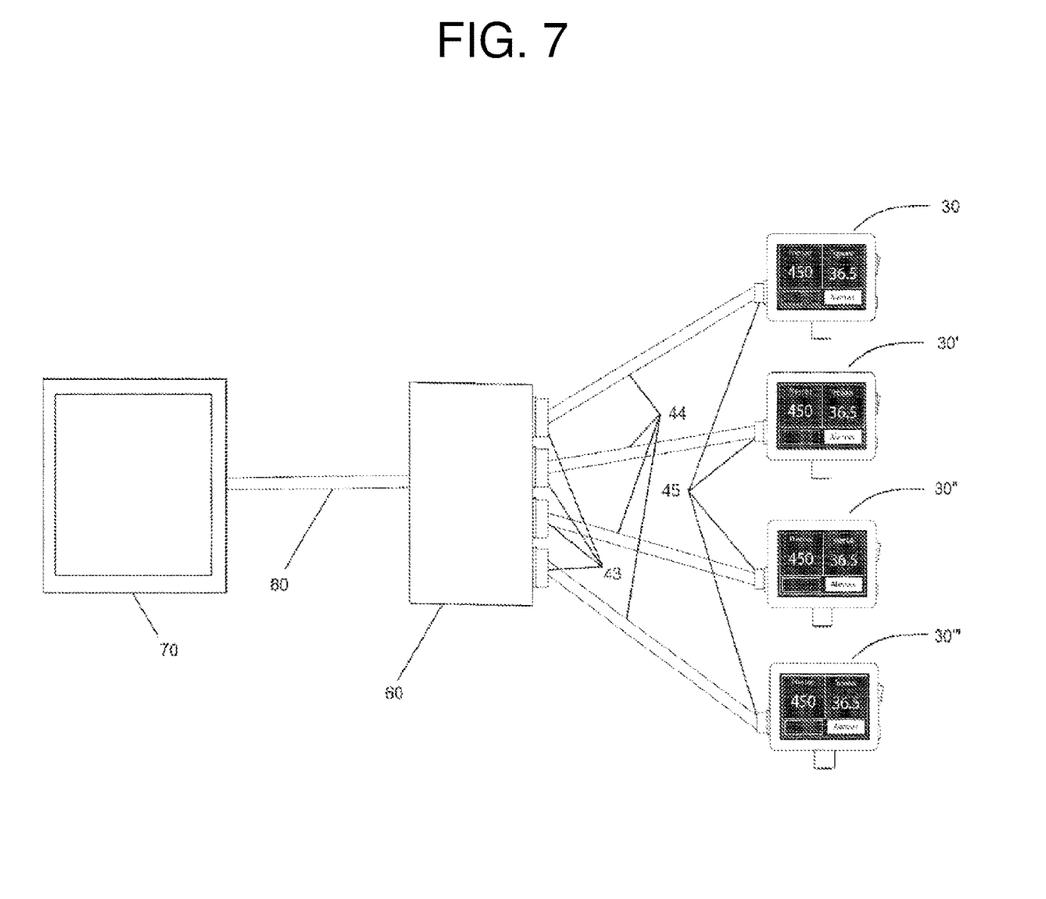
FIG. 7 is a schematic view of the alternative control module and video monitor assembly of the system object of the present invention.

Alternatively, the system according to the present invention may comprise a control module (60) and video monitor (70) assembly, as illustrated in FIG. 7. In this case, the central monitor (40), described for FIG. 6, is replaced with an external video monitor unit (70), connected via video cable (120) to the control module (60), which has control buttons (not shown) for interaction with the software of the remote monitor (70).

Several advantages to the system according to the present invention over conventional vital sign monitoring are checked, as follows.

Better Signal Quality:

Conventional monitors have analog electronics for amplifying and conditioning vital signs within the equipment and receive sensor signals over generally long cables. The signals coming from the sensors usually have very small amplitudes of the order of only a few microvolts. As a result, when transmitted through long cables which are generally in an environment full of interference, they lose quality and amplitude. In addition, analog electronics are close to the power supply and the CPU, which are major sources of electromagnetic interference. All of this requires the monitor to have sophisticated circuitry for signal amplification and filtering to retrieve the original signal. In the case of the minimonitor (30) according to the present invention, the pressure and temperature CPB transducer (110) is connected directly to the amplification circuit, and the power supply is external. As a result, we have an interference-free, lossless signal, and therefore of better quality, at the analog electronics input. This allows us to have a simpler amplification and filtering circuit, but without losing signal quality. In addition, the minimonitor (30) has a CPU that digitizes and processes the signal, displaying it on the built-in display and sending the already properly processed pressure and temperature values as a digital signal, practically interference-free, to the external monitor (40). Therefore, the external monitor (40) need not have any kind of analog electronics, as it only displays the values previously processed by the minimonitor (30). The result of all this is a much simpler and less costly system than current monitors, but with superior performance.

Simplicity and Robustness:

Due to its design, the system allows the use of very simple electronic circuits, but it provides superior performance to commercially available systems. In addition, because it is simpler, it becomes more robust and less prone to defects.

Modularity:

As explained above, the system is fully modular and can be scaled to meet user needs by simply adding new modules.

Flexibility:

The system can be tailored to the needs of each user or moment. For simple surgery, the user may choose to use only the CPB transducer (110) and minimonitor (30), or for more complex surgeries or procedures such as ECMO, may use multiple CPB transducers (110) coupled to respective minimonitors (30) and an external monitor (40) for viewing and controlling all parameters, in addition to alarms and other features. In addition, in case of cardiac surgery, for example with the control module (60)+video monitor (70) system, the control module (60) may be close to the perfusionist for ease of operation and ergonomics and the video monitor (70) may be at a higher position to allow viewing by other healthcare professionals present in the operating room. In the case of an ECMO, where the perfusionist works alone most of the time, the compact external monitor (40), which can be close to the center console, can be used for greater portability and ergonomics.

Practicality:

The system is very easy to use. For complete monitoring, simply install the CPB transducers (110) on the cardiopulmonary bypass circuit, attach and connect the minimonitors (30) to the respective CPB transducers (110) and connect the minimonitors (30) to the external monitor (40) through the communication cables (44). When the equipment is turned on, the system automatically begins to monitor the circuit parameters with no need for any additional procedures. There is no need to even zero or level the transducers.

Calculation of Hydraulic Resistance:

Calculating hydraulic resistance can be very useful in situations where it is wanted to evaluate the resistance change of a cardiopulmonary bypass circuit device throughout the procedure. For example, it is possible to verify the normal operation of an arterial filter or oxygenator by monitoring hydraulic resistance. To calculate the hydraulic resistance of a device, two pressure transducers and one flow transducer are required, the transducers must be installed one before and one after the device to be evaluated and the flow sensor must be installed on the same line next to the device. The calculation of the hydraulic resistance of the device is made by the equation below:

$$Rh=(Pe-Ps)/\text{flow}$$

wherein:
Rh=hydraulic resistance
Pe=Pressure at device inlet
Ps=Pressure at device outlet
Flow=total flow through the device Normally, a device's working check is done by assessing pressures and flow separately, but this assessment is complex and requires a great deal of user knowledge and experience. Analysis of hydraulic resistance, on the other hand, is much simpler and more straightforward, because it brings together the contributions of all other parameters into one value, making it much more sensitive and reliable and greatly facilitating parameter interpretation. That is, it is ok if the resistance remains constant during the procedure. If resistance begins to increase, it may indicate clogging or clotting in the device. If resistance begins to decrease, it may indicate leakage in the device. In addition, by using multiple transducers along the circuit at strategic points, such as, for example, before the oxygenator, after the oxygenator and after the arterial filter, it is possible, in case of changing the CPB parameters, to find out which device is having problems, before they become more serious.

Low Cost:

Because it has fewer components and simpler circuits, the cost of the system according to the present invention becomes much cheaper.

The invention claimed is:

1. A system for monitoring physiological parameters in cardiopulmonary bypass (CPB), the system comprising:
   a CPB transducer and
   a minimonitor,
   wherein the CPB transducer comprises a compartment having at least one disposable CPB sensor selected from a disposable pressure sensor and a disposable temperature sensor, a connection cable configured to connect the at least one disposable CPB sensor to the minimonitor, one electrical connector configured to connect and provide electrical power to the at least one disposable CPB sensor, a CPB housing having a hole configured to allow contact between the at least one disposable CPB sensor and a patient's blood, and one optional fitting, fitting; and
   wherein said minimonitor has an analog electronic circuit with an automatic zero system for amplifying and filtering signals from the at least one disposable CPB sensor and a CPU which digitizes and processes the analog signals for later viewing through the display on the equipment panel and digital transmission to an external display.

2. The system according to claim 1, wherein the at least one disposable CPB sensor is a disposable pressure sensor, and the electric connector connected to the disposable pressure sensor, via the connection cable, wherein said disposable pressure sensor is installed within the sensor housing and is configured for direct contact with a patient's blood through the hole in the housing.

3. The system according to claim 2, wherein the at least one disposable CPB sensor also includes a disposable temperature sensor.

4. The system according to claim 1, wherein the at least one disposable CPB sensor is a disposable temperature sensor and the electric connector is connected to the disposable temperature sensor, via the connection cable, and the disposable temperature sensor is installed within the sensor housing.

5. The system according to claim 3, wherein said CPB transducer uses the same electrical connector for the disposable pressure sensor and the disposable temperature sensor.

6. The system according to claim 1, wherein said minimonitor comprises a display for viewing pressure and/or temperature values and a user interface, an electrical connector for connection to the CPB transducer, a fitting for direct coupling to the CPB transducer or circuit tube, an auxiliary clamp fitting, a connector to an external power supply and a connector for the communication cable with an external monitor, and wherein the CPB transducer is directly coupled to the minimonitor.

7. The system according to claim 1, wherein the system comprises an external monitor capable of receiving data from a plurality of minimonitors (30, 30', 30", 30''') and exhibits said data at least one of graphically numerically, and synchronously.

8. The system according to claim 7, wherein said external monitor is compact and comprises a display and control buttons operating the display, connectors for digital communication cables and connectors for connection to the plurality of minimonitors.

9. The system according to claim 1, the system comprises a control module and video monitor assembly interconnected via video cable.

10. The system according to claim 1, wherein said housing has a fitting for securing the assembly to a suitable support.

* * * * *